United States Patent [19]

Mattiasson

[11] Patent Number: 4,592,994

[45] Date of Patent: Jun. 3, 1986

[54] METHOD FOR THE DETERMINATION OF BIOCHEMICAL DATA

[75] Inventor: Bo G. Mattiasson, Lund, Sweden

[73] Assignee: Alfa-Laval AB, Tumba, Sweden

[21] Appl. No.: 464,498

[22] PCT Filed: May 28, 1982

[86] PCT No.: PCT/SE82/00193

§ 371 Date: Jan. 28, 1983

§ 102(e) Date: Jan. 28, 1983

[87] PCT Pub. No.: WO82/04264

PCT Pub. Date: Dec. 9, 1982

[30] Foreign Application Priority Data

Jun. 4, 1981 [SE] Sweden ............... 8103520

[51] Int. Cl.$^4$ ............................................. G01N 33/50
[52] U.S. Cl. ............................................. 435/7; 435/29;
435/34; 436/149; 436/519; 436/810; 436/827
[58] Field of Search .................. 435/34, 39, 174, 287,
435/7; 436/810, 519, 149, 827

[56] References Cited

U.S. PATENT DOCUMENTS

| | | | |
|---|---|---|---|
| 3,403,081 | 9/1968 | Rohrback et al. | 204/1 |
| 3,843,324 | 10/1974 | Edelman et al. | 23/230 B |
| 4,054,491 | 10/1977 | Lindgren | 435/34 |
| 4,072,576 | 2/1978 | Arwin et al. | |
| 4,235,964 | 11/1980 | Bochner | 435/34 |
| 4,246,344 | 1/1981 | Silver | 435/39 |
| 4,288,544 | 9/1981 | Suzuki | 435/39 |
| 4,350,763 | 9/1982 | Suzuki | 435/34 X |
| 4,424,279 | 1/1984 | Bohn | 436/810 X |
| 4,425,438 | 1/1984 | Bauman | 436/810 X |

FOREIGN PATENT DOCUMENTS 2826416 12/1979 Fed. Rep. of Germany.
WO80/02849 12/1980 PCT Int'l Appl..

OTHER PUBLICATIONS

Methods in Enzymology, vol. 34, pp. 220–225, Ed. Jakoby W. B. Wilchek M. published 1974.
Proc. Nat. Acad Sci. USA, vol. 68, pp. 2153–2157, published 1971, "Cell Fractionation and Arrangement on Fibers, Beads & Surfaces", (Edelman G. M. et al.).
Biomed. Eng. vol. 9, pp. 18–20, published 1/74, "Rapid Detection of Bacterial Activity Using Impedance Measurements", UR A, Brown D. F. J. Dec. 8, 1984.
Chemical & Eng. News, pp. 29–35, published 1/27/75 (Rechnitz G. A.) "Membrane Bioprobe Electrodes".

*Primary Examiner*—Sidney Marantz
*Attorney, Agent, or Firm*—Davis Hoxie Faithfull & Hapgood

[57] ABSTRACT

Microorganisms and unicellular organisms in a sample are identified or determined by exposing the sample to an adsorbent having a specific binding power for the entity to be determined to bind the entity to the adsorbent, separating unbound sample, exposing the adsorbent containing the entity to a nutrient medium to initiate metabolism with resulting change in the physical or chemical characteristics of the substrate and observing these changes.

15 Claims, 9 Drawing Figures

FIG. 4a
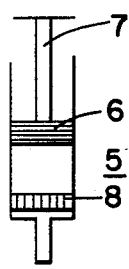
FIG. 4b
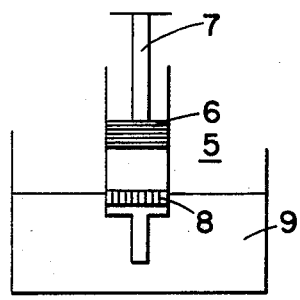
FIG. 4c
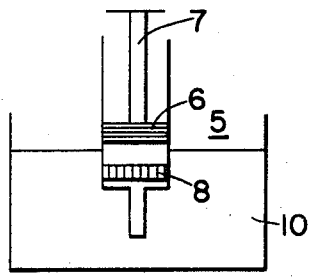
FIG. 4d
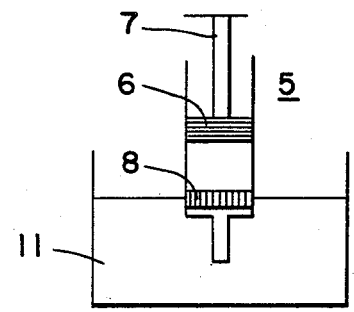
FIG. 4e
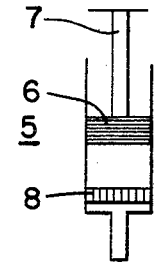
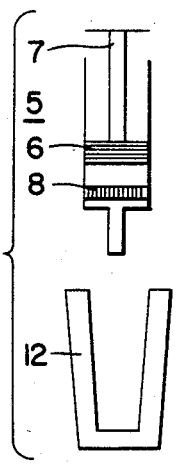
FIG. 4f

METHOD FOR THE DETERMINATION OF BIOCHEMICAL DATA

The present invention concerns a method for the determination of the content and species of microorganisms in a sample. There are already several different procedures to determine species and amount, but a common drawback with all these is that they require a long time, often several days to make one determination. To date workers have used a procedure involving plating, which means spreading, on a plate or glass surface, a layer of substrate to which is added the microorganisms whose number and species. At first nothing is seen in the medium, but later are to be determined on the microorganisms divide and eventually form a number of colonies that are observable by the naked eye. Based on the assumption that one cell creates one colony, the number of microorganisms are allowed to divide, the species of the microorganism can be determined. Another procedure to determine amount and kind of microorganism is to use specific sorbents containing antibodies. Such sorbents immobilize a predetermined species of microorganism against which the antibodies are directed. When the cells have been captured in this way they can be incubated in a growth medium, and when the microorganisms, through division, have given rise to a larger group of cells that is observable by the naked eye, the amount of microorganisms can be determined by colony counting. The choice of substrate to which the adsorbent with the microorganisms are added gives an indication of the kind of microorganisms that has been adsorbed, since only certain microorganisms are able to grow in a certain substrate, while others need a different substrate for their growth.

The present invention is aimed at creating a system of procedures by which it is possible to determine biochemical data concerning microorganisms within a short period of time, in many cases within two hours.

The procedure is based upon the use of an adsorbent for a preselected microorganism, where the sample from which the microorganism is bound together with the sorbent, is washed after the adsorption the in order to eliminate all non-specifically bound cells. The washed microorganisms bound to the sorbent are exposed to a substrate so that the cell metabolism is started. For this metabolism there is a need for certain substances concomittant with generation of metabolic products.

The quantity of generated products is directly related to the number of adsorbed cells. One or more products may be utilized either directly or indirectly to determine the amount of microorganisms. The species of the microorganisms is determined by the adsorbent due to its specific binding properties.

The adsorbent is as a rule a carrier provided with antibodies directed against the microorganisms that is to be adsorbed. If it is desirable to adsorb all microorganisms, then as an alternative either mixtures of antibodies or other binding structures with a broader specificity, eg. lectins are used.

The above mentioned substrate may be or may contain oxygen and the products may be eg. those generated by consumption of oxygen due to metabolic activity. The amount of oxygen consumed can be determined with established measuring equipment.

Other parameters may be the pH of the substrate-medium. The pH-value can be determined by using a pH-indicator and fotometric equipment.

Still another parameter is reduction equivalents formed during the metabolism. These reduction equivalents are uncoupled from the ordinary metabolism by eg. artificial electron acceptors, the degree of reduction of which can be determined by established technique.

Still another parameter may be the amount of carbon-dioxide generated during the metabolism, as this amount can be determined by using established analytical instruments.

Moreover, for certain types of cells specific metabolites may be excreted, the concentration of which in the medium can be used to determine the number of cells bound to the sorbent. Analysis in such a case is performed with a dedicated specific analysis developed for the individual metabolites.

Still another physical property of the medium that is changed during the metabolic events is the conductivity. By measuring same and the changes in conductivity over a certain time of incubation, the quantity of metabolizing cells or the degree of metabolic activity in a fixed number of cells can be determined.

The procedure according to the present invention can furthermore also be used to determine the concentration of certain biochemical products that in a clear way influences on the metabolism of the microbial cells.

Examples of such substances are vitamins and antiobiotics. Analyses of such substances are carried out using predetermined numbers of a specific microorganism which is bound to the sorbent.

When assaying the content of a vitamin in a nutrient, then microorganisms are bound to the sorbents that have an absolute requirement for the actual vitamin for their metabolism. The sample to be analysed is mixed with a full medium for the cells from which the substance to be analysed for has been omitted. Then, to the washed sorbent with adsorbed microorganism the substrate that is to be analysed is added. The degree of metabolic activity is dependent upon the amount of the vitamin present. By measuring metabolic activity for the cell preparations at known concentrations of vitamins, the metabolic activities registered can be used as reference values when the content in an unknown sample is to be evaluated from the calibration curve.

The procedure according to the invention can also be used to determine the influence of inhibiting substances on cell metabolism, eg. antibiotics. In this case the adsorbent is charged with a certain microorganism in a predetermined amount. Antibiotics are introduced together with a nutrient medium to a washed adsorbent with adsorbed microorganisms. After metabolic activity has occurred for a certain period of time, the change in concentration of metabolites can be read eg. as a change in pH-value and thus it is possible also to determine the amount antibiotics in the sample by comparative studies with a calibration curve which is obtained with known concentrations of antibiotics.

Additional characteristics of the present invention will appear below.

BRIEF DESCRIPTION OF THE DRAWINGS

The invention is described more in detail below with reference to the drawing wherein

FIG. 4 shows a simple unit for practically performing the present invention.

Figure 1:
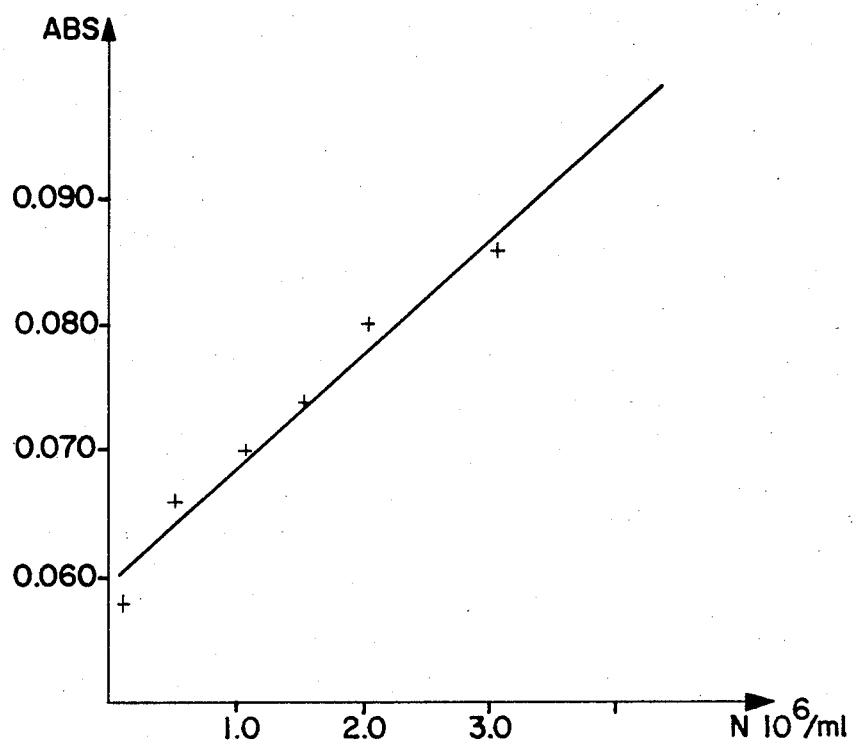
FIG. 1 shows a calibration curve for a predetermined microorganism, where the product generated, here read as change in absorbance, is plotted versus the number of microorganisms, N.

In the present invention it is essential pro primo, to use an absorbent to which cells are adsorbed, pro secundo to have a washing unit where the adsorbent with bound cells is washed to remove all unspecifically bound material and pro tertio to have a unit where adsorbed cells are supplied with nutrients so that cell metabolism can take place. This three-step system must, in order to be useful, be calibrated and this is done by constructing calibration curves from the behaviour of known amounts of known microorganisms. By constructing the curves, one uses the changes in physical parameters that take place as a result of the metabolism of the cells. These parameters may be acidity (read at pH-value), oxygen tension, redox-level, conductivity, concentration of a certain metabolite, carbon dioxide pressure etc.

One of the most useful parameters is the pH-value. To easily determine this a pH-electrode may be used, but in most cases a coloured pH-indicator has been used, the colour of which is related to the pH-value in the solution. Such pH-indicators may be of very different chemical structures. Several different ones have been used in this system. Examples of suitable substances are heptametoxired and phenolred. Usually the indicator is added to the nutrient medium and the nutrient medium used is analysed, usually spectrophotometrically. After the above mentioned three step procedure has been calibrated against known quantities of the species to be analysed, the analytical system can be used to primarily determine amount of a certain microorganism in a sample. The capture of the above mentioned predetermined microorganism is carried out by the use of a carrier-substance to which antibodies directed against the microorganism that shall be investigated are bound. As carrier is usually used a gel with a low tendency of unspecific adsorption of cells and other biological material. A frequently used carrier in such cases is Sepharose. The carrier must be modified by attacking an antibody to it—an antibody with specificity for the microorganism that shall be quantified in the analytical procedure. In certain cases it may also be of interest to collect the whole spectrum of microorganisms, and in that case a sorbent with the ability to adsorb microorganisms generally must be used. Such an adsorbent can be based on a binding structure of lectin-type, which is well-known, in many cases, to have a much broader substrate specificity than specific antibodies usually have.

If in a milieu, the amount of a certain microorganism is to be quantified, then an adsorbent is produced suitable for binding the specific microorganism. The adsorbent with its binding entities, either lectins or antibodies, is allowed to be in contact with the milieu where the microorganisms are present. After the absorbent has been exposed to the microorganisms for a given period of time, the sorbent is washed to remove unspecifically bound cells.

The washed sorbent with microorganisms is then supplied with nutrient, which can be a sugar solution with suitable buffering substances and eg. a pH-indicator, or some other liquid medium, in which the cells to be quantified can metabolize.

When the absorbent with the captured microorganisms is exposed to nutrient medium, metabolism starts and is allowed to proceed for a fixed number of minutes, usually 30–120. After incubation in the nutrient medium analysis is performed of the medium, usually by a spectrophotometer. Based on the value read in that analysis, it is possible, by consulting a calibration curve (FIG. 1), to determine the number of microorganisms of the selected species in relation to the numbers used as references when setting up the calibrated curve for a selected organism. In the case here described there has, been used as a parameter change in pH-value as a result of metabolic activity. In metabolism there is in many cases a demand for externally added oxygen. The amount of oxygen consumed can be determined and from this value it is possible to determine the number of cells by using a calibration curve similar to that in FIG. 1. In a similar way the number of redox-equivalents as well as the amount of carbondioxide generated by the metabolic activity can be determined. These values are directly related to the number of microorganisms.

The way in which the number of microorganisms discussed so far are quantified is generally by using laboratory equipment well-known to chemists. However, it is also possible to use the present invention in a more basic way. One prerequisite however is that a calibration curve of the type shown in FIG. 1 be available and that it is possible, by the use of charts with different colours or possibly by spectrophotometry, to quantify the change in colour that appears in the nutrient medium as a result of metabolism by the investigated microorganisms. The simplified method for quantification is illustrated in FIG. 4 with the subfigures 4a–4f.

In these figures is shown a disposable plastic syringe 5, with a piston 6, and a piston handle 7. Just in front of the tip of the syringe is placed a filter 8, eg. of nylon with holes of 25 μm. On top of the filter is placed the adsorbent equipped with antibodies or other binding structures directed against the microorganism to be quantified. The syringe 5 is dipped into a vessel 9, containing a fluid with the microorganisms to be quantified. The fluid with the microorganisms is sucked into the syringe 5, where the adsorbent captures that amount of microorganisms that it is capable of under the conditions used. Then the liquid is removed together with non-bound microorganisms and other impurities. This is done according to a washing procedure as illustrated in FIG. 4c. In 4d a nutrient medium is sucked into the syringe and mixed with the sorbent containing captured microorganisms. The nutrient medium may consist of a buffered glucose solution with suitable indicator-molecules or other substances.

After a sufficient amount of nutrient medium is drawn into the syringe 5, it is removed from the vessel 11. The nutrient medium is kept in the syringe 5, and is allowed to react for a certain time, usually between 30 and 120 minutes, sometimes shorter or longer. After this time period the syringe 5 is emptied of nutrient medium. The nutrient medium is added to a vessel 12 that preferentially is transparent. By measuring the colour of the nutrient medium the amount of microorganisms in the sample 9 can be determined.

Figure 2:
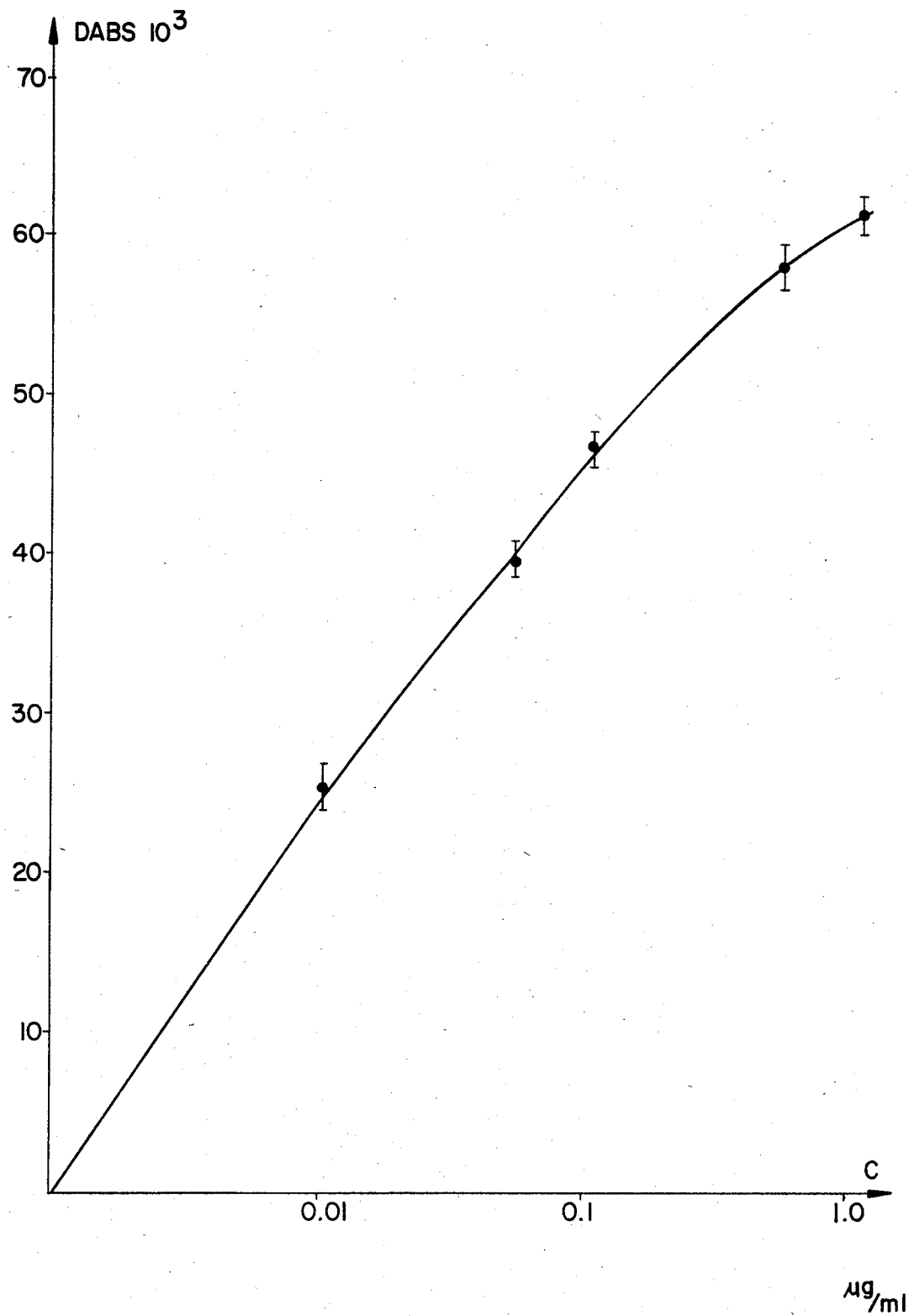
FIG. 2 shows a calibration curve valid for a predetermined vitamin, with the concentration of vitamin C plotted against measured change in absorbance after a given period of incubation of a predetermined number of cells.

The procedure according to the present invention can also be used to determine concentration of vitamin in a substrate. Hereby, the procedure involves the selection of a microorganism that needs an external supply of the vitamin of interest in order to be capable of maintaining metabolism. An adsorbent with such microorganisms is washed in the usual way and is then exposed to a nutrient medium that is a complete medium with the exception of the vitamin to be quantified, mixed with the sample to be analysed. The degree of metabolic activity is related to the content of vitamins in the sample. In this case also changes in pH-value can be utilized for determining metabolic activity and, thereby, via a calibration curve, the vitamin content. To simplify the procedure a calibration curve must be constructed according to FIG. 2 which can be used to evaluate the vitamin content by measured colour intensity.

Figure 3:
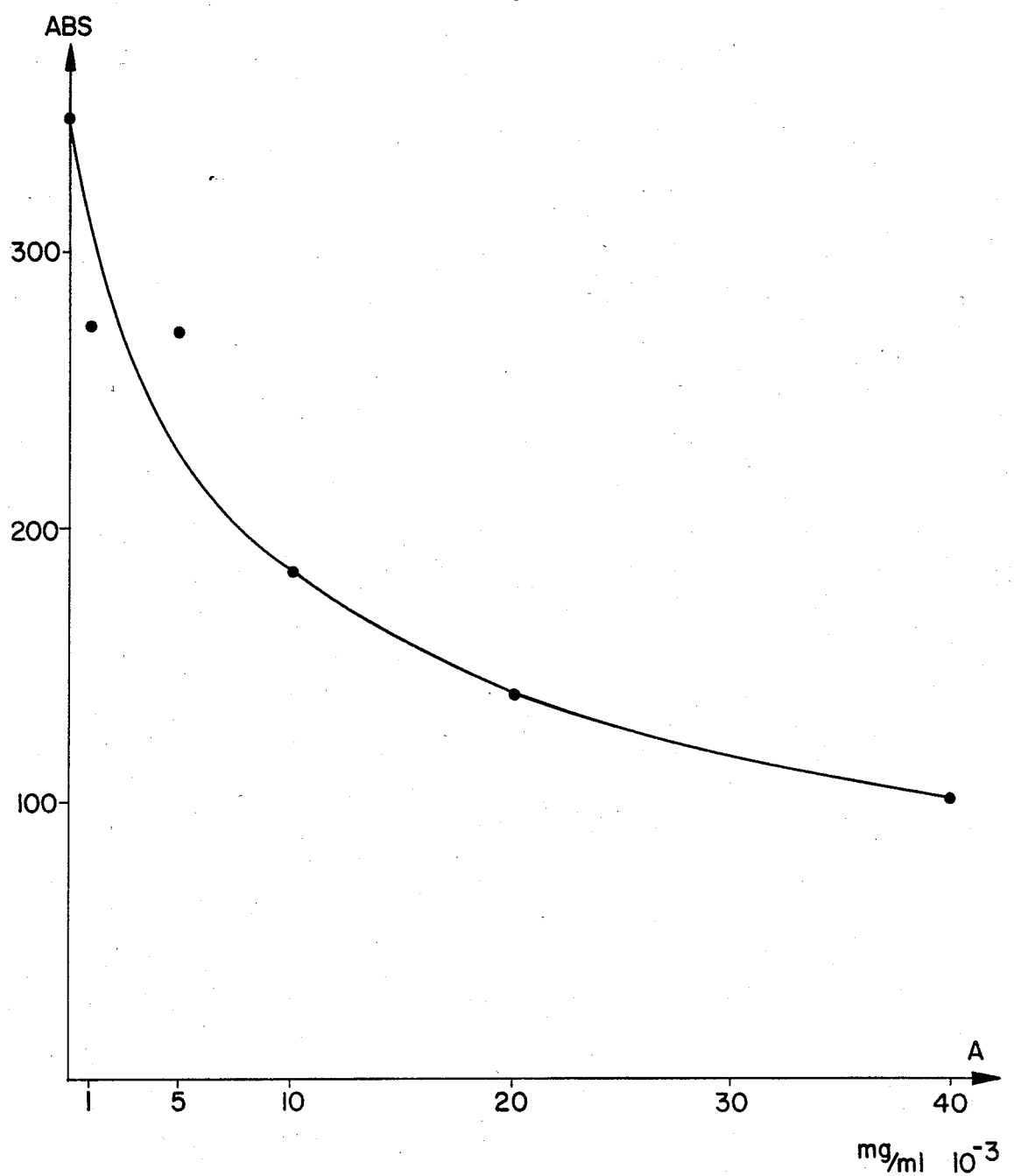
FIG. 3 shows a calibration curve valid for a predetermined antibiotic and where the absorbance read is plotted versus concentration of antibiotic in the sample A.

The assay unit according to the present invention can also be used to determine the concentration of a known antibiotic by studying the influence by various samples containing antibiotic on the metabolism of various microorganisms. In this procedure, the adsorbent is exposed to, and thus can adsorb a predetermined number of microorganisms. After washing of the exposed adsorbent to remove all cells not properly bound, it is treated with a nutrient medium in combination with an antibiotic. Metabolism starts operating, but it will be inhibited due to the fact that the antibiotic to a certain extent inhibits the activity of the microorganisms. After a certain time of exposure, which usually is between 30 and 120 minutes, the colour intensity of the nutrient medium can be read and thereby the influence of the antibiotic can be evaluated. In FIG. 3 is shown a calibration curve obtained from using a certain number of cells incubated in media containing varying concentrations of the antibiotic to be quantified. Translation of values obtained on unknown samples can be done by using a calibration curve. As a further information from such a test, the pattern of resistance for the microorganism can be determined.

All cells contain ATP. This fact can be used to determine the number of cells in a sample. By using the above mentioned adsorption technique the cells are bound to a specific adsorbent. The bound cells are then treated so that ATP is released to the medium surrounding the sorbent. The amount of released ATP has been shown empirically to be correlated to the number of cells. By addition of the enzyme-substrate system luciferas—luciferin a light signal can be obtained that can be related to the amount of ATP in the sample and thus to the number of cells in the primary sample.

This latest described application concerns still another important area of application of general interest, namely concentration of cells from a sample to a small volume in order to obtain a sensitive and accurate analysis.

EXAMPLE 1 (COUNTING OF YEAST CELLS)

A disposable plastic syringe (2 ml) equipped with a 25 μm-filter in front of the outlet is supplied with 1 ml Concanavalin A-Sephadex. Then ½ ml of sedimented Concanavalin A Sepharose (either prepared by ourselves according to established procedures or bought from Pharmacia Fine Chemicals AB, Uppsala, Sweden) is suspended in 2 ml buffer, pH 7.4 (0.004 mM $KH_2PO_4$, 0.054 mM Tris, 0.41 mM $NaHCO_3$, 0.95 mM $CaCl_2$, 0.80 mM $MgSO_4$, 5.36 mM KCl, 137 mM NaCl) and poured into the syringe. The piston is then introduced and the air is emptied before the excess of liquid is forced out. The sample to be analysed is sucked into the syringe. A total of 2 ml of sample is sucked in. Incubation is carried out for 10 minutes to allow the cells to bind to the gel. During incubation the content of the syringe is mixed gently by turning the syringe end-over-end with time intervals of 1-3 minutes. After this incubation, the solution is forced out of the syringe and 2 ml of buffer is sucked in. The solution is forced out again. This washing procedure is repeated 4 times before 2 ml of substrate is sucked in after which the syringe is shaken so that a homogeneous suspension is obtained. The excess of substrate is emptied so that 0.8 ml (total volume=substrate+gel) remains in the syringe.

The substrate solution consists of a buffer having the composition given above, supplied with glucose to a final concentration of 50 mM and neutral red to a final concentration of 0.2 mg/ml. By the addition of indicator to the medium pH must be adjusted to the initial value.

Incubation is carried out for 2 hrs in a water bath at 26° C. During this time period mixing is achieved by intermittent shakings of the syringe.

After the incubation period, the substrate solution was forced out of the syringe and collected in a collecting vessel. The absorbance at 528 nm was read.

| cell number | change absorbance |
|---|---|
| $4-10^4$ | 0.054 |
| $7-10^4$ | 0.057 |
| $1.1-10^5$ | 0.078 |
| $1.5-10^5$ | 0.085 |
| $2.2-10^5$ | 0.088 |
| $2.5-10^5$ | 0.095 |
| $7.5-10^5$ | 0.107 |
| $1.0-10^5$ | 0.119 |

EXAMPLE 2

Concentration and counting of yeast cells in various diluted solutions

In this example a 2 ml disposable plastic syringe was used in which 0.5 ml Concanavalin-S-Sepharose had been packed according to the procedure described in the previous example. This small column was used in this example of application as an adsorbent through which the solution to be analysed was drawn with a constant speed. Standard solutions with varying dilutions of yeast cell suspensions were prepared by diluting a yeast cell suspension with the buffer described in Example 1.

The volume of the sample sucked into the sorbent was adjusted with respect to the cell number, so that in total an equally large number of cells were introduced in the Concanavalin A-Sepharose column. When the cell suspension had been drawn through the column, incubation was allowed to proceed for 10 minutes thereby giving possibilities for the creation of strong so called multi-point attachment bonds. The experimental procedure followed that given in Example 1, In the experiment, except for the blank experiment, 6 milj cells were sucked into the sorbent.

| No of cells per ml | Absorbance at 528 nm |
|---|---|
| 0 | 0.020 |
| 0.1 milj | 0.080 |
| 0.2 | 0.116 |

-continued

| No of cells per ml | Absorbance at 528 nm |
| --- | --- |
| 0.6 | 0.115 |
| 1.2 | 0.120 |
| 6 | 0.122 |

EXAMPLE 3

Quantification of thiamin by yeast cells

The practical details in essence follow that given in Example 1, however, with another buffer, substrate and indicator. Furthermore, the condition of the cells in the starting moment is quite different. They are grown on Difcos special medium for thiamine assay. (The cells were grown for two days according to Difcos manual).

Buffer: 0.1M sodium acetate/acetic acid pH 4.5 containing also 0.95 mM $CaCl_2$, 0.81 mM $MgSO_4$, 5.36 mM KCl, 137 mM NaCl and 1.0 mM $MnCl_2$.

Indicator: Bromophenylblue dissolved in the same buffer, 4 mg/l.

Thiamine-solution: After capturing the cells by the Concanavalin A-Sepharose, the syringe was filled (2 ml/syringe) for 30 minutes with a thiamine solution or a sample solution where the content of thiamin was to be determined. Incubation was carried out at 37° C. with regular mixing. The thiamin solution was afterwards washed out through 2 repeated washings with buffer.

To each syringe was then added substrate, 50 mM glucose in buffer with indicator 4 mg/L. Incubation for 2 hrs at 37° C. under gentle mixing. The substrate solution is emptied and $A_{585}$ is read.

| Thiamine μg/ml | $A_{585}$ |
| --- | --- |
| 0 | 0 |
| 0.1 | 0.0253 |
| 0.05 | 0.040 |
| 0.10 | 0.047 |
| 0.50 | 0.0585 |
| 1.0 | 0.062 |

EXAMPLE 4

Quantification of E. coli cell

The basic experimental procedure was the same as given in Example 1.

Buffer used: $CaCl_2$, 0.95 mM, KCl 5.35 mM, NaCl 137 mM, $MgSO_4$ 0.80 mM, $KH_2PO_4$ 0.004 mM $NaHCO_3$ 0.04a mM Tris 0.053 mM, pH 7.4.

Indicator: Neutralred 0.2 mg/ml substrate: 50 mM glucose in the above buffer.

In a 2 ml disposable syringe was added 0.5 ml Sepharose 4B to which was coupled antibodies with binding specificites against *Hemophilus influencae*, but also a certain activity against *E. coli*. The coupling technique used is known (C. Borrebaeck, J.Börjesson and B. Mattiasson, Clin. Chim. Acta 86, (1978) 267–278). Incubation for 20 minutes was used. After washing with buffer incubation with substrate and indicator took place for 2 hrs at 37° C. Then the absorbance was read at 528 nm.

| Number of cells | $A_{528}$ |
| --- | --- |
| $1 \cdot 10^6$ | 0.030 |
| $2 \cdot 10^6$ | 0.058 |
| $3 \cdot 10^6$ | 0.080 |
| $4 \cdot 10^6$ | 0.103 |
| $5 \cdot 10^6$ | 0.110 |

EXAMPLE 5

Quantification of amphotericin

Quantitation of amphotericin is done by measuring the inhibiting effect of amphotericin on metabolic response from immobilized cells.

The procedure follows Example 1, with the exception that 6 ml cells were used and exposed to varying concentrations of amphotericin for 20 min prior to incubation in substrate.

| Amphotericin μg/ml | A |
| --- | --- |
| 0 | 0.067 |
| 2 | 0.055 |
| 4 | 0.051 |
| 8 | 0.042 |
| 16 | 0.038 |
| 32 | 0.041 |

I claim:

1. A method for the identification or determination of an entity selected from the group consisting of microorganisms and unicellular organisms in a sample which comprises:
    (a) exposing the sample to an adsorbent having a specific binding power for said entity to bind said entity to said adsorbent;
    (b) separating unbound sample from the adsorbent;
    (c) exposing the adsorbent with bound entity to a nutrient-containing substrate to initiate metabolism of the entity, thereby causing the substrate to change its chemical or physical characteristics; and
    (d) observing the changes of chemical or physical characteristics of the substrate caused by the metabolic process.

2. The method of claim 1, wherein the adsorbent contains immobilized lectins.

3. The method of claim 1, wherein the adsorbent contains immobilized antibodies.

4. The method of claim 1, wherein the changes in the pH of the substrate resulting from the metabolic process are observed.

5. The method of claim 1, wherein the oxygen consumption in the substrate resulting from the metabolic process is observed.

6. The method of claim 1, wherein a redox reaction in the substrate resulting from the metabolic process is observed.

7. The method of claim 1, whereby the production of $CO_2$ in the substrate resulting from the metabolic process is observed.

8. The method of claim 1, whereby the electrical conductivity of the substrate resulting from the metabolic process is observed.

9. A method for the identification or determination of a substance in a sample which comprises adding to the sample an entity selected from the group consisting of microorganisms and unicellular organisms whose metabolism is influence by said substance, said entity being bound to an adsorbent having a specific binding power for said entity, bringing the sample with the added entity into contact with a nutrient-containing substrate to initiate metabolism of said entity, thereby to cause chemical or physical changes in the substrate, and observing said changes.

10. The method of claim 9, characterized in that a pH change, caused by the metabolism, is determined.

11. A method claim in claim 9, characterized in that oxygen consumption, caused by the metabolism, is determined.

12. The method of claim 9, characterized in that redox status is determined for the reduction equivalents that are produced by the metabolism.

13. The method of claim 9, characterized in that $CO_2$ produced by the metabolism is determined.

14. The method of claim 9, characterized in that a change in electrical conductivity, caused by the metabolism, is determined.

15. A method for the identification or determination of an entity selected from the group consisting of microorganisms and unicellular organisms in a sample which comprises:
 (a) introducing the sample into a vessel containing an adsorbent with a specific binding power for said entity, to bind said entity to said adsorbent;
 (b) removing unbound sample from said vessel;
 (c) introducing a fluid nutrient medium into said vessel;
 (d) maintaining said nutrient medium in contact with said adsorbent and the entity bound thereto to initiate metabolism of said entity;
 (e) removing the nutrient medium from the vessel and observing the effects of said metabolism on said removed medium.

* * * * *

UNITED STATES PATENT AND TRADEMARK OFFICE
CERTIFICATE OF CORRECTION

PATENT NO. : 4,592,994

DATED : June 3, 1986

INVENTOR(S) : Bo G. Mattiasson

It is certified that error appears in the above—identified patent and that said Letters Patent is hereby corrected as shown below:

Column 1, line 14, after "number and species" insert --are to be determined--; line 15, after "later", delete "are to be determined"; line 44, after "adsorption" delete "the".

Column 3, line 50, "attacking" should be --attaching--; line 65, "absorbent" should be --adsorbent--.

Column 4, line 6, "absorbent" should be --adsorbent--; line 15, "calibrated" should be --calibration--.

Column 8, line 10, "Quantitation" should be --Quantification--.

Signed and Sealed this

Seventeenth Day of March, 1987

Attest:

DONALD J. QUIGG

Attesting Officer

Commissioner of Patents and Trademarks